US006281351B1

(12) United States Patent
Robyt et al.

(10) Patent No.: US 6,281,351 B1
(45) Date of Patent: Aug. 28, 2001

(54) LINEAR AND CYCLIC SUCROSE REACTION PRODUCTS, THEIR PREPARATION AND THEIR USE

(75) Inventors: John F. Robyt; Rupendra Mukerjea, both of Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/072,459

(22) Filed: May 5, 1998

Related U.S. Application Data

(62) Division of application No. 08/687,813, filed on Jul. 24, 1996, now Pat. No. 6,075,139.

(51) Int. Cl.$^7$ .............................. C07H 11/04; C07H 3/04
(52) U.S. Cl. .................... 536/115; 536/123; 536/123.13; 127/46.1
(58) Field of Search ................................. 127/15, 16, 29, 127/30, 46.1, 47, 64; 536/115, 123, 123.13, 127

(56) References Cited

U.S. PATENT DOCUMENTS

| | | | |
|---|---|---|---|
| 2,927,919 | 3/1960 | Anderson | 260/209 |
| 3,170,915 | 2/1965 | Gaertner | 260/210 |
| 3,300,474 | 1/1967 | Flodin | 260/209 |
| 3,870,664 | * 3/1975 | Faulkner | 260/9 |
| 4,380,476 | 4/1983 | Mufti et al. | 127/46.3 |
| 5,128,248 | * 7/1992 | Dordick et al. | 435/100 |
| 5,270,421 | 12/1993 | Dordick et al. | 527/311 |
| 5,270,460 | * 12/1993 | Dordick et al. | 536/115 |
| 5,498,709 | 3/1996 | Navia et al. | 536/124 |
| 5,618,933 | * 4/1997 | Dordick et al. | 536/115 |
| 5,854,030 | * 12/1998 | Dordick et al. | 435/72 |

FOREIGN PATENT DOCUMENTS 1 543 167    3/1979   (GB) .

OTHER PUBLICATIONS

"Sucrose—Properties and Applications", edited by Mathlouthi and Reiser, publ. by Blackie Academic & Professional, pp. 266–267, 1995.*

"Sucrose Chemicals—A critical review of a quarter–century of research by the Sugar Research Foundation", by Valerie Lollonitsch, publ. by The International Sugar Research Foundation, pp. 88, 89, 158, 159, 1970.*

Black et al., Alkali Metal Derivatives of Sucrose. II.* Condensation of Sodium Sucrates with Organic Halogen Compounds, J. Appl. Chem., vol. 9, pp. 256–265, May 1959.*

McKeown et al.—Selective Substitution in Sucrose—Canadian Journal of Chemistry, vol. 35, 1957, pp. 28–36.

Fairclough et al.—Derivatives of β–D–Fructofuranosyl α–D–Galacto–Pyranoside—Carbohydrate Research, 40 (1975) 285–298.

Bolton, et al.—Sucrochemistry—Part 1. New Derivatives of Sucrose Prepared from the 67,6'Di–O–Tosyl and the Octa–O–Mesyl Derivatives—Carbohyd. Res., 21 (1972) 133–143.

Chowdhary, et al.—Sucrochemistry. Part 33. The Selective Pivaloylation of Sucrose—J. Chem. Soc. Perkin Trans. I 1984, pp. 419–427.

Hirano et al.—Phosphorylated Glycans Produced from Non-reducing Mono–and Oligosaccharides by the Action of $P_2O_5$ in Dimethyl Sulfoxide and Their Interactions with Concanavalin A—Agr. Biol. Chem., 39 (10), 1963–1967, 1975.

Communications to the Editor—Journal of the American Chemical Society /87:30/ Oct. 20, 1965, pp. 4651–4652.

Khan—Chemistry of New Uses of Sucrose: How Important?—Pure & Appl. chem., vol. 56, No. 7, pp. 833–844, 1984.

Synthetic Polymers Containing Sugar Residues v. Polyesters Derived from D–Cellobiose and Dicarboxylic Acid Chlorides by Direct Polycondensation—Journal of Polymer Science: Polymer Chemistry Edition, vol. 18, 365–370 (1980).

Morris et al.—Experimental Chemical Shift Correlation Maps from Heteronuclear Two–Dimensional NMR Spectroscopy . . . 1. Carbon–13 and Proton Chemical Shifts of Raffinose and Its Subunits—J. Am. Chem. Soc. 1981, 103, 4703–4711.

Reactions of Aliphatic Acid Chlorides—N.O.V. Sonntag, Chem. Revs. 52 (1953) pp. 321–324.

Silver and Silver Alloys to Sulfolanes and Sulfones—Kirk–Othmer—Encyclopedia of Chemical Technology—Third Edition, vol. 21—pp. 921–948. (1983).

Chem. Ber. 17 (1884).
Chem. Ber. 19 (1886).
Chem. Ber. 23 (1890).
Ann. Chemie 265 (1891).
Chem. Ber. 53 (1920).

* cited by examiner

*Primary Examiner*—Kathleen Kahler Fonda
*Assistant Examiner*—Leigh C. Maier
(74) *Attorney, Agent, or Firm*—McDermott, Will & Emery

(57) ABSTRACT

Sucrose ester and ether products, useful as food or beverage bulking agents, reduced calorie sweeteners, fat replacement agents, stabilizing agents, thickening agents and emulsifying agents; adhesives; biodegradable plastics and films; sizing agents for paper and textiles; ethical pharmaceuticals and new fibers are prepared by using a two-phase reaction system in which sucrose is dissolved in an alkaline, aqueous solution and an acidic reagent such as a bifunctional acid dichloride or epoxide is added to the sucrose in a water-immiscible organic solvent. Several types of products are produced: water-insoluble sucrose ester (ether) copolymers; water-soluble sucrose ester (ether) copolymers; sucrose ester (ether) dimers; and intramolecular, cyclic sucrose esters (ethers). These products can be further varied by using different kinds of acid dichlorides or epoxides that contain different kinds of functional groups. The reaction proceeds at the interface of the water/organic solvent solutions whereby there is imparted a specificity that restricts the reaction to the 6 and 6' primary alcohol groups of sucrose. The reactions can be selected for each of the four basic types of products by controlling the various reaction parameters.

13 Claims, No Drawings

LINEAR AND CYCLIC SUCROSE REACTION PRODUCTS, THEIR PREPARATION AND THEIR USE

This application is a division of application Ser. No. 08/687,813 filed Jul. 24, 1996, now U.S. Pat. No. 6,075,139.

FIELD OF THE INVENTION

This invention relates to new and useful sucrose derivatives, the particular methods for their syntheses, and the use of the products.

BACKGROUND OF THE INVENTION

The most abundant pure organic chemical in the world is sucrose. See Kirk-Othmer, *Encyclopedia of Chemical Technology*, 3d Edition, Volume 21, John Wiley & Sons, New York, pages 921–948 (1983). However, although sucrose produced from sugar cane and sugar beets is ubiquitous in its availability and is of relatively low cost, only a fraction of a percent by weight is consumed as a chemical feedstock. The potential value of sucrose as a raw material has been recognized for many years and has been the subject of considerable research.

Sucrose is a particularly appropriate material for use in the formation of esterified products produced currently from petroleum-based materials because (a) it is a naturally occurring, relatively abundant renewable material; (b) it is polyfunctional with three reactive primary alcohols that can readily be derivatized; (c) it is a nonreducing sugar and thus does not have the potential for the wide variety of side-reactions that reducing sugars have; (d) it has a relatively easily hydrolyzed glycosidic linkage that allow sucrose polymers to be potentially more biodegradable than polymers made with other carbohydrates, such as sugar alcohols; and (e) it is a naturally occurring sweet carbohydrate in common use and therefore potentially useful in the formation of potential non-absorbable, noncaloric sweeteners.

The usual technique for the synthesis of carbohydrate esters involves a reaction of the carbohydrate with an acid chloride or acid anhydride in a basic organic solvent, such as triethylamine, pyridine or quinoline. In a few instances, the organic base has been replaced by sodium hydroxide. However, the prior art teaches very little about the reaction of sucrose with polyfunctional reagents.

Although relatively few successful derivatives of sucrose have been commercialized, there has been substantial interest in developing sugar-based synthetic technology. Thus, in 1953, Sonntag, in *Chemical Reviews* 52 at page 321, described a technique where a polyhydroxy compound was dissolved in a large excess of a tertiary amine, and by adding thereto an acid chloride, preferably in a solvent such as chloroform. However, only mixtures in low yields were obtained which were not easy to separate.

On the other hand, the preparation of pure regiospecific esters of polyhydric alcohols (carbohydrates) is a more complicated problem requiring special innovation, such as prior to reaction, the blocking of certain hydroxyl groups in the polyalcohol with easily removable groups.

In the patented literature, U.S. Pat. No. 2,927,919 relates to ether-esters of sucrose, U.S. Pat. No. 3,170,915 discloses sucrose ethers and U.S. Pat. No. 3,300,474 discloses the preparation of sucrose ether co-polymerizates.

SUMMARY OF THE INVENTION

It is accordingly one object of the present invention to provide a new group of ester and ether derivatives of sucrose.

It is a further object of the invention to provide a novel class of sucrose esters and ethers which are useful as food bulking agents, reduced calorie sweeteners, fat replacement agents for food products, stabilizing agents for food and beverage products, thickening and emulsifying agents for food products, adhesives, biodegradable plastics and films, sizing agents for paper and textiles, ethical pharmaceuticals and new fibers.

A still further object of the present invention is to provide a method for the preparation of sucrose esters which enables preparation of the sucrose esters in high yields and with improved specificity over methods known to the prior art.

Other objects and advantages of the present invention will become apparent as the description thereof proceeds.

The present invention comprises the use of various bifunctional reagents such as dicarboxylic acid dichlorides, epichlorohydrin, phosphorus oxychloride, and diphosphoryl tetrachloride for the formation of sucrose derivatives. The sucrose products disclosed herein are embraced by the following formula:

Suc—R(—Suc—R—)$_x$Suc wherein Suc is a sucrose molecule attached to a connector group R at the 6,6-, 6,6'-, or 6',6'-positions of the sucrose in which x ranges from 0 up to about 500, and R is a radical which is the residue of a bifunctional acidic reactant. Preferably, R is a hydrocarbylacyl or hydrocarboyloxy radical or a phosphorous radical wherein the hydrocarbylacyl portion may be saturated or unsaturated aliphatic, cycloaliphatic, or aromatic, and may be further substituted by one, two, three or more other groups such as amino, hydroxyl, halogen, alkyl, alkyl substituted amino, or the like. By hydrocarbylacyl is meant a hydrocarbon portion of the type specified having two carbonyl functional groups attached to sucrose.

Preferably R is a radical selected from the group consisting of:

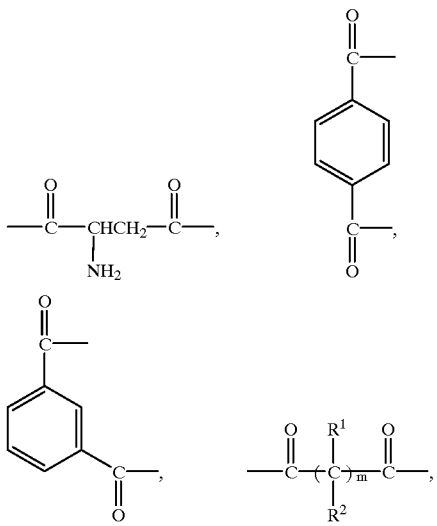

-continued

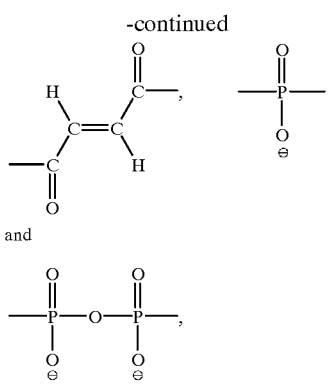

and and the corresponding alkali metal and alkaline earth metal salts wherein m is 0 up to about 10, preferably 0 to about 6, and each of $R^1$ and $R^2$ independently is H, or $C_1$–$C_4$ alkyl or one of $R^1$ and $R^2$ can also be OH or $CH_2OH$.

To prepare the sucrose derivative of this invention, sucrose is reacted with a bifunctional reactant preferably of the formula X—R—X, wherein R is as defined above and X is a functionally reactive group such as a halogen, under special reaction conditions as described hereinafter. The preferred halogen is a chlorine group. The reaction is performed by the slow addition of a bifunctional reagent such as an acyl dichloride, dissolved in a substantially water immiscible organic solvent, to an alkaline aqueous solution of sucrose. The reaction proceeds at the interface between the two immiscible solutions to provide an interfacial condensation and produce the sucrose derivative or analogue. It has been discovered that this reaction at the interface of the organic solution and the aqueous solution imparts a specificity to the reaction for the 6 and the 6' primary alcohol groups of sucrose.

It should be understood that equivalent reactants such as diepoxides and halohydrocarbyloxiranes such as epichlorohydrin also react in the process to provide new and useful sucrose esters.

It is a feature of the invention that the reaction can be controlled to produce at least four different types of compounds: a water-insoluble polymer, a water-soluble polymer, a sucrose dimer and a cyclic sucrose adduct. The relative amounts of each of these compounds can be selected by adjusting the conditions of the reaction. By the use of selected reaction conditions, yields of up to 95 to 100% of the desired product may be obtained. By appropriate selection of the type of acidic reactant, different structural groups with various chemical properties can be incorporated into the resulting sucrose compounds.

These sucrose reaction products have a wide range of potential uses as food bulking agents, reduced calorie sweeteners, fat replacement agents for food products, stabilizing agents for food and beverage products, thickening and emulsifying agents for food products, adhesives, paper and textile sizing, biodegradable plastics and films, ethical pharmaceuticals, and new fibers. When applied in these areas, the sucrose reaction products are combined with a non-reactive carrier in amounts of about 1 wt. % up to 99 wt. %.

DETAILED DESCRIPTION OF THE INVENTION

The present invention discloses reactions of certain acidic reagents with sucrose, the latter having the following structure and numbering system for the reactive hydroxyl groups and corresponding carbon atoms:

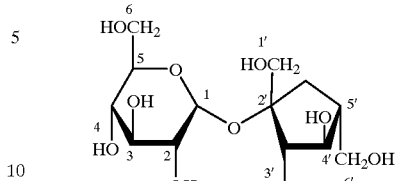

Formula 1

Sucrose

By the present invention it has been discovered that conducting the reaction of sucrose with a bifunctional acidic reactant or epoxide as described herein enables one to obtain specificity of the reaction at the 6 and 6' positions of sucrose. The resulting products are novel sucrose condensation products wherein sucrose molecules are linked together by ester or ether linkages which may either be linear or cyclic and which in general represent a new class of sucrose products having a wide variety of uses.

An especially novel feature of the invention concerns the method by which the sucrose products of the present invention are produced. According to the invention, it has been discovered that sucrose condensation products comprising sucrose molecules linked at the 6,6'-; 6,6-; 6',6'-positions, or mixtures thereof, to the bifunctional acidic reactant reactant, are produced in high yields and purity by conducting the reaction with two immiscible solvents. The process is conducted generally by dissolving the appropriate amount of sucrose in a slightly alkaline aqueous phase and then adding slowly thereto a bifunctional acidic reactant contained in an organic solvent.

The type of product to be produced can be controlled as desired by varying reaction conditions such as molar ratios of reactants, rates of addition, or other reaction conditions as will be described hereinafter.

The preparation of at least four general types of products are described herein, designated as P1, P2, P3 and P4. These products are obtained from the reaction of sucrose with a bifunctional acidic reactant such as dicarboxylic acid dichlorides. The reaction is conducted with two immiscible solvents, a slightly alkaline water-phase containing sucrose, and a substantially water-immiscible organic phase using preferably halogenated solvents or aromatic solvents such as methylene chloride, chloroform, carbon tetrachloride, aromatic solvents such as benzene, toluene, or (m-, p-, or o-) xylene containing the acid reactant such as an acyl dichloride. Any organic solvent that is substantially water immiscible and will dissolve the acidic reactant is generally operable in the invention. The organic solution containing the acidic reactant is added slowly, such as dropwise, over various time periods with stirring and maintenance of the pH between 8 and 9 by the addition of an aqueous alkali metal hydroxide such as sodium hydroxide.

It should be understood that the process for reaction of sucrose with bifunctional reagents disclosed herein has wide applicability to the production of new sucrose reaction products. The concept of conducting the reaction at the interface of two immiscible solvents containing the reactants provides a novel and effective procedure for producing sucrose reaction products with the unexpected result of avoiding the substantial formation of unwanted products.

The reaction is exemplified by the reactions and products described herein but is not limited thereto.

As indicated above, at least four different general types of products described herein are produced by the process of the invention. These products have different structures and different characteristics.

Thus, the product designated P1 herein is a substantially water-insoluble polymer of the formula:

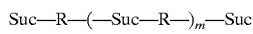

Suc—R—(—Suc—R—)$_m$—Suc where Suc is a sucrose molecule, R is as defined above, and m has a value of about 100–500.

The product designated herein as P2 is a water-soluble polymer and may be designated by the following formula:

Suc—R—(—Suc—R—)$_n$—Suc wherein n has a value of about 20–50. This polymer is a much lower molecular weight polymer than the product P1.

The product designated as P3 is a linear sucrose dimer which may be designated by the following formula:

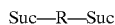

Suc—R—Suc where Suc and R are as defined above.

The product designated herein as P4 is a cyclic sucrose product in which the connecting group R is contained within the cyclic ring of the product formed. The chemical structures of these products in generalized form are shown hereinafter.

As noted above, P1 is the designation for a water-insoluble product that precipitates from solution as the reaction proceeds. P2 is a water-soluble product that can be precipitated from solution by the addition of a solvent such as an alcohol, e.g., 1 to 1.5 volumes of ethanol. Neither of these products is chromatographically mobile by Thin Layer Chromatography (TLC). A third product, P3, can also be selectively produced in relatively high yields. It is mobile on TLC, but migrates more slowly than P4. Both P3 and P4 are water-soluble, but not precipitated by 2 volumes of ethanol. Both are mobile on TLC, migrating just behind sucrose. P3 and P4, therefore, are low molecular weight compounds while P1 and P2 are polymeric compounds of differing molecular weights. Reaction conditions can be adjusted to favor the formation of P1 and P2. Likewise, conditions can be selected to produce P3 or P4 in 95 to 100% yield and high purity.

All four types of products are produced herein in the preferred embodiment by the reaction of an alkaline aqueous solution of sucrose with an acid dichloride contained in a water-immiscible solvent. Suitable acid dichlorides comprise oxalic acid dichloride, malonic acid dichloride, succinic acid dichloride, glutaric acid dichloride, adipic acid dichloride, pimelic acid dichloride, suberic acid dichloride, fumaric acid dichloride, malic acid dichloride, glutamic acid dichloride, terephthalic acid dichloride, isophthalic acid dichloride, and other such reagents as epichlorhydrin, phosphorus oxychloride and diphosphoryl tetrachloride. Use of this wide variety of acidic reactants will generate large numbers of different sucrose condensation products. The ability to use a wide variety of bifunctional acidic reactants enables the incorporation of diverse structural groups with corresponding properties to the resultant sucrose compounds.

Generalized structures are shown below in Formula 2 for the P1 and P2 products where m is 100 to 500 for P1 and n is 20 to 50 for P2. Generalized structures for P3 and P4 are also shown.

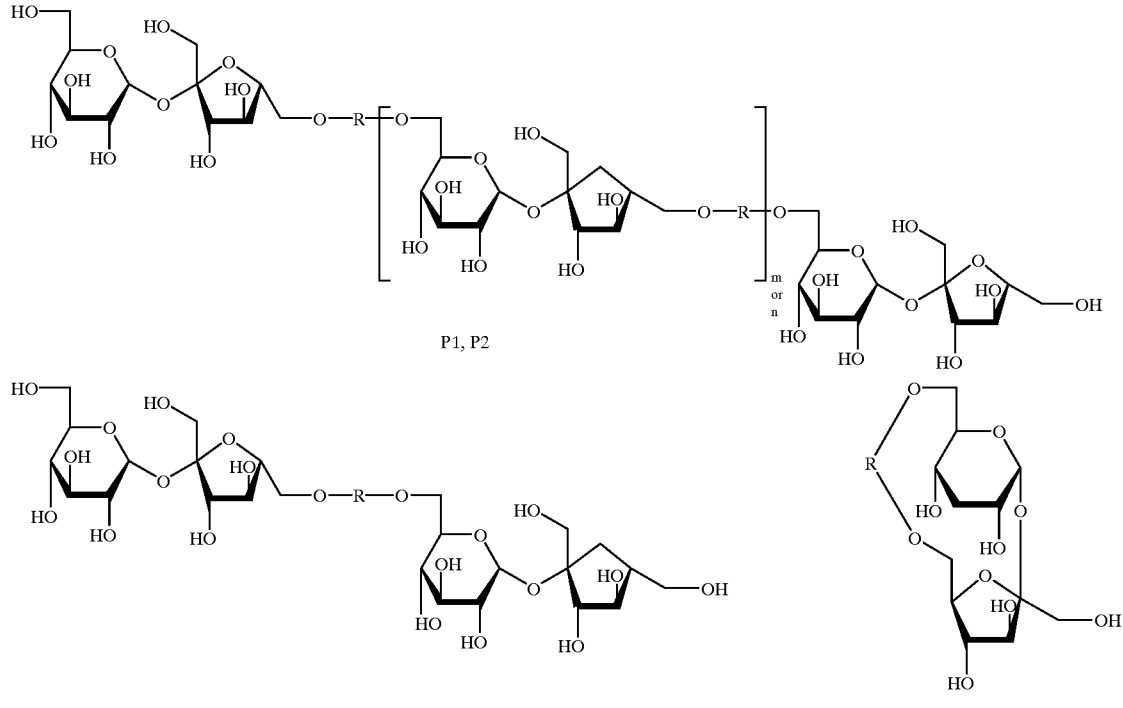

Formula 2

Generalized Structures for Sucrose-Acid Dichloride
Reaction Products P1, P2, P3 and P4

Structure of P1

Reaction of the P1 products with sodium methoxide in methanol gives a quantitative conversion to sucrose, indicating that P1 contains intact sucrose and that the sucrose is not hydrolyzed or cleaved into glucose and fructose during the reaction. Because of the water-insolubility and the reaction conditions (relatively dilute solutions of acid dichloride and higher temperatures) that favor P1, it is postulated that P1 is a relatively high molecular weight, linear copolymer of sucrose and the diacid. Further, because of the higher reactivities of the 6 and the 6' hydroxyl groups of sucrose compared with its other hydroxyl groups, it is postulated that the linkage of the dicarboxylic acid is between these two hydroxyl groups, as shown for the 6,6'-isomer in Formula 2. The polymer is believed to be linear based on the knowledge that branched polysaccharides with relatively high molecular weights are water-soluble. Branching of high molecular weight carbohydrate polymers is known to impart water-solubility to these polymers. For example, amylopectin (5% branching) and B-512F dextran (also 5% branching) are water-soluble, whereas amylose, a nonbranched or only slightly branched $\alpha$-1→14 glucan, is water-insoluble.

Structure of P2

P2 products on the other hand, are also linear, but of lower molecular weight than P1. The P2 products are water-soluble and precipitatable from aqueous solution by the addition of one to two volumes of ethanol. P2 is believed to be the water-soluble precursor of P1, having a structure like P1, but with a lower molecular weight.

Structure of P3

The P3 product obtained from the reaction of sucrose with succinyl dichloride, SP3, where S is succinyl, has a TLC migration less than that of SP4, indicating that it is of higher molecular weight. It is also non-reducing and converts to sucrose when treated with sodium methoxide in methanol, showing that the compound contains intact sucrose. The $^{13}$C-NMR of the chlorinated SP3 shows four carbon resonances shifted downfield for C-4, C-6, C-1' and C-6', evidencing chlorination at these positions. The spectrum also gives two resonances for C-6 -and C-6' that are not significantly shifted downfield, revealing that not all of the 6 and 6' carbons are substituted with chlorine and are esterified as the succinate. Thus, the proposed structure for SP3 is 6,6'-disucro-succinate. The synthesis of P3 appears to be the first product in the polymerization reaction leading to the formation of P2 and P1. There could be three possible isomers for P3. Using SP3 as an example, there are produced 6,6'-disucro-succinate; 6,6-disucro-succinate; and 6',6'-disucro-succinate, based on the $^{13}$C-NMR of the chlorinated product. A mixture of these isomeric linkages would not alter the type of $^{13}$C-NMR spectrum produced for the chlorinated product. The same types of isomers would also be expected to occur in P1 and P2.

Structure of P4

The P4 product from the reaction of sucrose with a bifunctional acidic reactant such as an acid dichloride is a low molecular weight product as judged by TLC migration. For example, the reaction of sucrose with succinic acid dichloride under conditions favoring production of P4 results in a product (SP4) eluting just behind the void volume on a Bio-Gel P2 column. It does not have any reducing power and is completely converted to sucrose on treatment with sodium methoxide in methanol. This shows that intact sucrose is present with succinic acid in an ester linkage. SP4 consumes three moles of periodate per mole of sucrose (mole of sucrose determined using phenol-sulfuric acid analysis, using sucrose as a standard). This is compatible with the ester linkages at the 6 and 6' positions of a single sucrose molecule.

A $^{13}$C-(proton decoupled)-NMR spectrum of SP4 is very similar to the $^{13}$C-NMR spectrum of sucrose. Nevertheless, it is not sucrose as evidenced by its TLC migration which is different from that of sucrose. Also, it is not converted into glucose and fructose by invertase and does not have a sweet taste. Other investigators have reported that esters of carbohydrates do not significantly shift the 13C-NMR carbon resonances of the carbohydrate. To circumvent this problem and establish the structure of the P4 products, SP4 was chlorinated with sulfuryl chloride under conditions reported to give chloro-substitution of sucrose at positions 1', 4, 6 and 6'. [Ballard, et al., *J. Chem. Soc. Perkin Trans. I*, 1524 (1974).]

Chlorinated sucrose gives a $^{13}$C-(proton-decoupled) NMR spectrum in which the resonances for C-1', C-4, C-6 and C-6' are shifted downfield from the resonances obtained for sucrose indicating the substitution of chlorine at these positions. The $^{13}$C-NMR spectrum for chlorinated SP4 shows significant downfield chemical shifts (15–20 ppm) only for C-4 and C-1' and only slight downfield chemical shifts (5–6 ppm) for C-6 and C-6'. These latter, minor chemical shifts for C-6 and C-6' can be explained by the differences between the two solvents used, $D_2O$ for SP4 and $CDCl_3$ for chlorinated SP4. The use of the two different solvents is necessitated by differences between the solubilities of SP4 and its chlorinated product. The $^{13}$C-NMR chemical shifts for the chlorinated SP4 product indicate that C-4 and C-1' are chlorinated and C-6 and C-6' are not chlorinated. These results indicate that the position of esterification of succinic acid in SP4 is indeed at C-6 and C-6' of the sucrose. The structure of SP4 is confirmed to be 6,6'-succinyl sucrose, an intramolecular cyclic ester.

Thus, structural studies on SP4 and similar P4 products of this invention show: (1) they are low molecular weight compounds; (2) they do not have any reducing power; (3) they are completely converted to sucrose by sodium methoxide in methanol; (4) they consume 3 moles of periodate added thereto per mole of sucrose; (5) they give $^{13}$C-NMR spectra very similar to that of sucrose; 6) chlorination of these products give $^{13}$C-NMR spectra consistent with the formation of intramolecular cyclic esters (ethers) substituted at the 6,6'-positions and (7) treatment of these products with invertase does not afford glucose or fructose and results in compounds that do not migrate from the origin on TLC analysis.

Because of the similarity in the method of synthesis and in the physical characteristics of water solubility and TLC mobility, the structures of four general types of compounds formed by reaction of sucrose with each of several bifunctional acid chlorides (i.e., oxalyl, malonyl, succinyl, glutaryl, adipyl, pimelyl, fumaryl, suberyl, malyl, glutamyl, terephthaloyl, isophthaloyl, phosphoryl and pyrophosphoryl) are of the same structural type. That is, P1 is a relatively high molecular weight, linear copolymer of the individual acid linked to C-6 and C-6' of sucrose in a repeating structure; P2 is a lower molecular weight, linear copolymer of similar structure; P3 is a linear saccharide of two sucrose molecules linked through their 6 and 6' positions to the acids; and P4 is a cyclic intramolecular ester (ether) of the individual acid (epoxide) and the C-6 and C-6' positions of sucrose. The properties of the individual compounds, therefore, depend on the structure of the products (P1, P2, P3 and P4) and the nature of the individual acidic residue incorporated in the compound. That is, the properties are dictated by the number of methylene groups, unsaturation, phosphoryl groups or pyrophosphoryl groups, or other substituents, etc. of the acid (epoxide) in the molecule and the sites of the linkages between the acid (epoxide) and the sucrose molecules. For most of the syntheses, the preferred molar ratio of acid dichloride (epoxide) to sucrose is 1.2:1.0. An almost exclusive synthesis of P4 is obtained by using a more dilute solution of the acid dichloride (epoxide) in the organic solvent than that used for a synthesis designed to generate P1 plus P2 plus P4. This is accomplished by increasing the volume of the organic solvent to obtain the correct molar ratio and adding it over a period of about 60 minutes instead of about 15 minutes. Also, a nearly exclusive synthesis of P3 is obtained by using a molar acid dichloride (epoxide) to sucrose ratio of 1:2 and adding the acid dichloride (epoxide) in an organic solvent to the sucrose solution at about 40° C. over a period of about 30 minutes.

Crystalline P4 products

Three crystalline P4 products have been synthesized, these products resulting from the reaction of sucrose with succinic acid dichloride, adipic acid dichloride and phosphorus oxychloride. Although the three compounds are not identical, all three appear to be hexagonal plates. In the case of 6,6'-adipyl sucrose, the plates associate or aggregate to give pyramid-like crystals.

The processes of the present invention differ from those of the prior art by utilizing a reaction involving a separation of the reactants into two phases, an alkaline-aqueous phase and a water-immiscible organic phase. This has led to a selectivity of the reaction with specific hydroxyl groups of sucrose, giving in most instances a single product in high yield. The isolation and purification of the product is facilitated by the product occurring in either one of the two phases, depending on the particular reaction. Accordingly, the solvent for sucrose is the alkaline-aqueous phase and the solvent for the particular derivatizing agent (acid dichloride, for example) is in the organic phase. The present processes eliminate the need to use water-soluble amines, such as pyridine, quinoline, or other amines that are detrimental to the use of the processes or products. The processes also eliminate the need, in most instances, for other expensive and sometimes noxious aprotic solvents, such as dimethylformamide, dimethylsulfoxide, or hexamethylphosphoramide. The organic phase is preferably a chlorinated solvent such as carbon tetrachloride or an aromatic solvent such as toluene, or other readily available organic solvent in which sucrose is insoluble and the bifunctional derivitizing agents are soluble.

In conducting the reaction, the solution of the bifunctional derivatizing agent in the organic phase is added slowly over a period of up to about one hour, such as dropwise, to an aqueous alkaline solution of sucrose to produce a sucrose derivative easily recovered from the aqueous phase. Further, the organic phase can be separated and recycled for use in subsequent reactions.

Process Parameters

The conditions of the reactions determine the types of products that are formed. The use of acid dichlorides (epoxides) as the bifunctional derivatizing agents gives four distinct products (P1, P2, P3, and P4), depending on the type, the concentration, the temperature, and the rate of addition of the derivatizing agent in the organic phase.

Sucrose added to the aqueous phase is utilized in a concentration of about 5 wt. % up to the limit of solubility of the sucrose at the temperature used. Ordinarily, a concentration of 5–50% is employed. Likewise, the reactant in the organic phase is employed in a concentration of about 5 wt. % up to the limit of its solubility in the solvent at the temperature used, but preferably using a concentration in the range of 5–50 wt. %. To obtain specific derivatives, the concentration may be varied by increasing the amount of organic solvent and/or by decreasing the rate of dropwise delivery of the reactant to the alkaline solution of sucrose or similar product.

While the ratios of reactants are ordinarily stoichiometric, the organic phase reactant to sucrose ratios may be from 1:2 to about 4:1, preferably about 1.2:1 to 2.2:1. Alkali is provided at a concentration of 0.05 to 5 molar, preferably 0.1 molar. The reaction takes place in a relatively short period of time, such as one half hour to 3 hours. However, occasionally the reaction is continued overnight. This is possible because room temperature is suitable for conducting the reaction, although 0° to 80° C., preferably 5° to 50° C., is also useful.

In the reaction, the products P1 and P2 will be produced together. P1 can be separated from any of the other products by centrifugation or filtration, as P1 is insoluble in most solvents. P2 is precipitated from the aqueous portion of the reaction mixture by adding two volumes of an alcohol such as ethanol to the solution after P1 has been separated.

The products, P1 and P2, are preferably prepared using a molar ratio of acid dichloride to sucrose of 2:1 to 4:1, with an optimum of 3:1, at a temperature range of about 15° to 25° C., with an optimum of about 20° C.; at a pH of about 7.5 to 10.5 with an optimum of about 8.5; and a rate of addition of the acid dichloride dissolved in the organic solvent in the range of about 15 to 45 minutes with an optimum of dropwise addition over a period of about 30 minutes.

The product, P3, is preferably prepared using a molar ratio of acid dichloride to sucrose of about 1:2 to 1.5:2, with an optimum of 1.2:2; at a temperature range of about 15° to 25° C., with an optimum of about 20° C.; at a pH of about 7.5 to 10.5, with an optimum of about 8.5; and a rate of addition of the acid dichloride dissolved in the organic solvent in the range of about 45 to 75 minutes, with an optimum of dropwise addition over a period of about 60 minutes.

The product, P4, is prepared using a molar ratio of acid dichloride to sucrose of about 1:1 to 1.5:1, with an optimum of 1.2:1; at a temperature range of about 15° to 25° C., with an optimum of about 20° C.; at a pH of about 7.5 to 10.5, with an optimum of about 8.5; and a rate of addition of the acid dichloride dissolved in the organic solvent of about 45 to 75 minutes, with an optimum of dropwise addition over a period of about 60 minutes.

The aqueous phase is separated from the organic phase and the product is recovered by evaporating the aqueous phase by vacuum rotary evaporation, or similar techniques, whereupon a syrup is produced. The syrup may then be triturated with acetone and ethanol to obtain a dry solid or it may be allowed to stand at room temperature for periods up to one to two weeks, whereupon crystals are formed.

The influence of changes in parameters, such as molar ratios of acid to sucrose, are shown by the results in the following table:

TABLE

REACTION CONDITIONS FOR THE REACTION OF SUCROSE WITH ACID DICHLORIDES

| REACTION CONDITIONS | MOLAR RATIOS ACID DICHLORIDE: SUCROSE | PRODUCT(S) |
|---|---|---|
| I. 20 g sucrose in 10 mL 0.1M NaOH; 10.86 g succinyl $Cl_2$ in 25 mL $CCl_4$ added dropwise over 30 min at 18° | 1.2:1 | SP1, SP2, SP4 |
| II. 20 g sucrose in 10 mL 0.1M NaOH; 10.86 g succinyl $Cl_2$ in 50 mL $CCl_4$ added dropwise over 60 min at 18° | 1.2:1 | SP4 |
| III. 40 g sucrose in 20 mL 0.1M NaOH; 21.72 g succinyl $Cl_2$ in 25 mL $CCl_4$ added dropwise over 30 min at 40° | 1.2:1 | SP1, SP2, SP3, SP4 |
| IV. 40 g sucrose in 20 mL 0.1M NaOH; 10.86 g succinyl $Cl_2$ in 25 mL $CCl_4$ added dropwise over 60 min at 18° | 1:2 | major SP3, trace SP4 |
| V. 40 g sucrose in 20 mL 0.1M NaOH; 28.5 g isophthaloyl $Cl_2$ in 100 mL $CCl_4$ added dropwise over 60 min at 18° | 1.2:1 | thick ppt. iPP1, iPP4 |
| VI. 40 g sucrose in 20 mL 0.1M; NaOH 28.5 g isophthaloyl $Cl_2$ in 100 mL $CCl_4$ added dropwise over 60 min at 40° | 1.2:1 | iPP1 ppt formed, but not as thick as as in V, +iPP4 |

Additional objects and advantages of the present invention will become readily apparent to those skilled in the art from the following examples, wherein only the preferred embodiment of the invention is shown and described, simply by way of illustration of the best mode contemplated for carrying out the invention. As will be realized, the invention is capable of other and different embodiments, and its several details are capable of modifications in various obvious respects, all without departing from the invention. Accordingly, the complete disclosure is to be regarded as illustrative in nature, and not as restrictive.

EXAMPLE 1

Synthesis of SP1, SP2 and SP4 (S=succinyl)

Sucrose (200g) was dissolved in 100 ml of 0.1M sodium hydroxide to give a 5.85M solution. Sufficient succinic acid dichloride was dissolved in 250 mL carbon tetrachloride to give a molar ratio of acid dichloride to sucrose of 1.2:1.0. The acid dichloride/carbon tetrachloride solution was added dropwise to the alkaline sucrose solution over 30 minutes with stirring at 22° C. The pH of the sucrose solution was maintained between 7 and 9 by the addition of 10%(w/v) sodium hydroxide. When all the carbon tetrachloride solution had been added, the reaction was stirred for an additional 15 minutes and 2 volumes of water were then added. The carbon tetrachloride layer was removed and the insoluble material (SP1) was filtered off. Ethanol (1–1.5 volumes) was added to the aqueous solution, giving a precipitate (SP2) that was removed by filtration. The remaining aqueous ethanol solution was rotary evaporated to a syrup, giving product SP4. Each of the products was triturated with anhydrous acetone 3 to 4 times and then with ethanol to give a free-flowing solid.

EXAMPLE 2

Synthesis of SP4 (S=succinyl)

Synthesis of 95 to 100% SP4 was accomplished by the reaction and procedures of Example 1 with the exceptions that the concentration of the acid chloride in the carbon tetrachloride was reduced to one-half by doubling the volume of carbon tetrachloride (to 500 mL in the above example), the reaction was conducted at 15° C. instead of 22° C., and the time of addition was increased to 60 minutes. The pH was maintained between 7 and 9. After addition was complete, the reaction mixture was stirred for an additional 30 minutes. Then two volumes of water were added, the carbon tetrachloride was removed, and the aqueous solution was rotary evaporated to a syrup. The syrup was triturated with acetone and ethanol as in Example 1, to obtain a solid or it was allowed to stand at room temperature for one to two weeks, whereupon crystallization occurred.

EXAMPLE 3

Synthesis of SP3 (S=succinyl)

To produce 95% SP3, sucrose (200 g) was dissolved in 100 mL of 0.1M sodium hydroxide. Sufficient succinyl dichloride was dissolved in 125 mL carbon tetrachloride to give a molar acid dichloride to sucrose ratio of 1:2. The carbon tetrachloride solution was added dropwise to the sucrose solution at 40° C. over a period of 30 minutes. The pH was maintained between 7 and 9. When the reaction was complete, as judged by the end of acid formation, two volumes of water were added, the carbon tetrachloride was removed, and the aqueous solution was rotary evaporated to a syrup. The syrup was triturated with acetone and ethanol as described in the above examples.

EXAMPLE 4

Synthesis of P4 by the reaction with oxalyl dichloride (OP4 where O=oxalyl)

The reaction conditions were essentially the same as for SP4 described above (Example 2) with the exception that the sucrose solution was kept at 5° C. during the addition of the oxalyl dichloride/carbon tetrachloride solution over a period of 30 minutes. After all the carbon tetrachloride solution had been added, the reaction mixture was allowed to warm to 15° C. and stirred at this temperature for 15 minutes. It was thereafter allowed to warm to 22° C. for an additional 15 minutes. The work-up of product OP4 was the same as described in Example 2.

EXAMPLE 5

Synthesis of P4 by the reaction with phosphorus oxychloride or diphosphoryl tetrachloride (PhP4 and Pyph P4 where Ph=phosphorous and Pyph=diphosphoryl)

The reaction conditions were the same as for OP4 described above with the exception that the phosphorus oxychloride or diphosphoryl tetrachloride solution was added to the sucrose solution at 5° C. over a period of 60 minutes. The work-up of products PhP4 and PyphP4 was the same as described for OP4 above. In the syntheses of Example 5, the pH was maintained between 7 and 9 by the addition of aqueous sodium hydroxide. The reaction was allowed to proceed until no more acid was formed. Before product work-up, the pH was adjusted to 7.0.

In most syntheses, carbon tetrachloride was used as the water-immiscible organic solvent, but toluene or other solvents as described could be substituted with similar results.

EXAMPLE 6

Four different basic kinds of products can, thus, be obtained (P1, P2, P3, and P4). In addition, each of the four products can be made from different acid chlorides (epoxides), each giving different chemical properties to the four products, depending on the particular acid chloride (epoxide). The number of possible products, thus, would be 4×n, where n is the number of types of acid chlorides (epoxides). For example, if eight different acid chlorides were used, there would be a total of 32 different kinds of possible esters. As examples, some of the different kinds of products can be differentiated in the following way:

OP1, OP2, OP3, OP4 where O is oxalyl

SP1, SP2, SP3, SP4 where S is succinyl

AP1, AP2, AP3, AP4 where A is adipoyl

MP1, MP2, MP3, MP4 where M is malonyl

FP1, FP2, FP3, FP4 where F is fumaryl

PP1, PP2, PP3, PP4 where P is phthaloyl

PhP1, PhP2, PhP3, PhP4 where Ph is phosphoryl

PyphP1, PyphP2, PyphP3, PyphP4 where Pyph is pyrophosphoryl,

EpiP1, EpiP2, EpiP3, EpiP4 when Epi is 2-hydroxy-1,3-propandiyl, where again P1, P2, P3, P4 represents the four types of general products that can be formed.

EXAMPLE 7

Synthesis of Cyclic 6,6'- (2-hydroxy-1,3-propandiyl) Sucrose by Reaction with Epichlorohydrin Sucrose (20 g, 58.4 mmol) was dissolved in 10 mL of 0.1 M NaOH. Epichlorohydrin (6.5 g, 70 mmol) was dissolved in 50 mL of toluene and added dropwise to the sucrose solution at room temperature over 30 min with constant stirring. The pH of the reaction mixture was maintained between 8–10 by the addition of 20% (w/v) NaOH. After all of the epichlorohydrin solution had been added, the reaction mixture was allowed to stir for another 30 min. The two phases were then separated. The aqueous phase was neutralized to pH 7 and then rotoevaporated to a syrup, with salts separating out. The syrup was allowed to stand at room temperature for 3–4 days when crystalline needles appeared and increased over the next several days.

The cyclic products P4 of Example 7 can be prepared using a reactant such as epichlorhydrin or a bifunctional acidic reactant as described herein (Examples 2 and 4–6). These reactants and the resulting products are illustrated in the following structural formula:

(A) acid dichloride in toluene (or chloroform) added dropwise to sucrose in 0.1 M NaOH

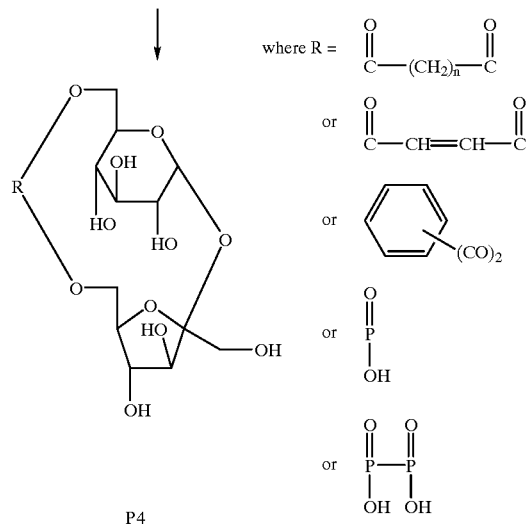

Formula 3

Reaction of sucrose in 0.1 M NaOH with an acid dichloride (B) epichlorohydrin in toluene (or chloroform) added dropwise to sucrose in 0.1 M NaOH

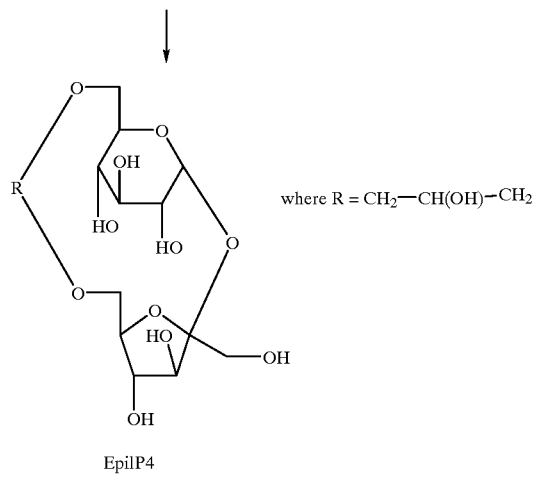

Formula 4

Reaction of sucrose in 0.1 M NaOH with epichlorohydrin

The invention has been described herein with reference to certain preferred embodiments. However, as obvious variations thereon will become evident to those skilled in the art, the invention is not to be considered as limited thereto.

What is claimed is:

1. A sucrose ester (ether) of yhe formula:

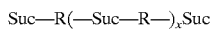

wherein Suc is a sucrose molecule attached to a container group R via a hydroxyl group at the 6,6-, 6,6'-, or 6',6'- positions of the sucrose molecule and x ranges from 20 to 50 and wherein R is selected from the group consisting of:

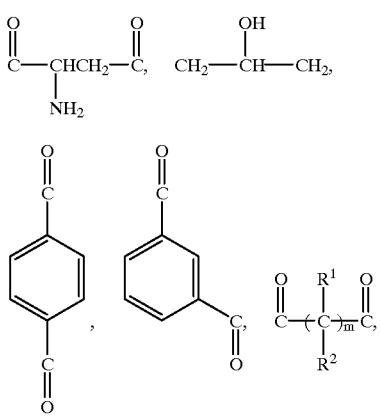

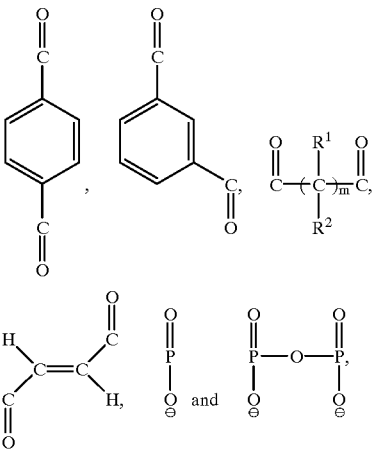

and the corresponding alkali and alkaline earth salts, and wherein m=0–10, and each of $R^1$ and $R^2$ independently is H or $C_1$–$C_6$ alkyl and one of $R^1$ and $R^2$ optionally is OH or $CH_2OH$.

3. A compound of the following formula:

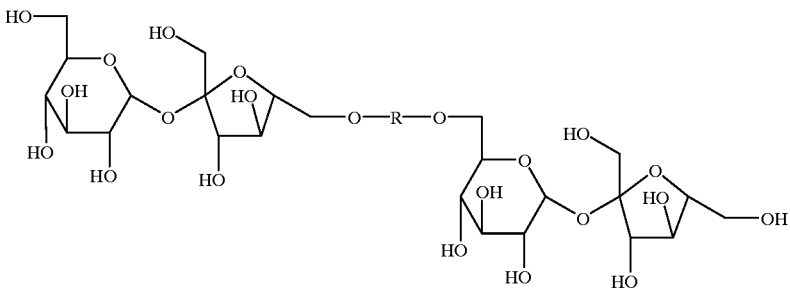

wherein R is a reactant selected from the group consisting of

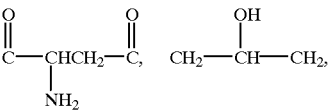

-continued

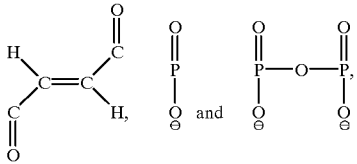

and the corresponding alkali and alkaline earth salts, and wherein m=0–10, and each of $R^1$ and $R^2$ independently is H or $C_1$–$C_6$ alkyl and one of $R^1$ and $R^2$ optionally is OH or $CH_2OH$, and the ester (ether) is a water soluble oligomer.

2. A sucrose ester (ether) of the formula:

Suc—R(—Suc—R—)$_x$Suc wherein Suc is a sucrose molecule attached to a connector group R via a hydroxyl group at the 6,6-, 6,6'-, or 6',6'-positions of the sucrose molecule and x is 0 and wherein R is selected from the group consisting of

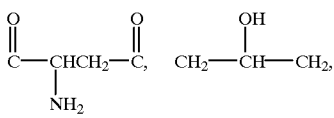

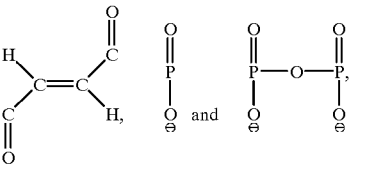

and the corresponding alkali and alkaline earth salts, and wherein m=0–10, and each of $R^1$ and $R^2$ independently is H or $C_1$–$C_6$ alkyl and one of $R^1$ and $R^2$ optionally is OH or $CH_2OH$.

4. The compound of claim 3, wherein R is

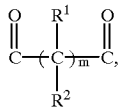

5. The compound of claim 4, wherein m is 0 to 8 and each of $R^1$ and $R^2$ is H.

6. The compound of claim 4, wherein m is 1, $R^1$ is OH and $R^2$ is H.

7. The compound of claim 4, wherein m is 1, $R^1$ is H and $R^2$ is $CH_2OH$.

8. The compound of claim 4, wherein m is 0.

9. The compound of claim 3, wherein R is

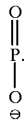

10. The compound of claim 3, wherein R is:

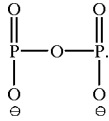

11. The compound of claim 3, wherein R is:

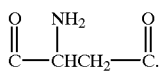

12. The compound of claim 3, wherein R is:

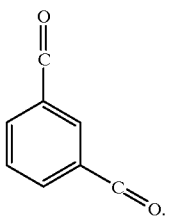

13. The compound of claim 3, wherein R is:

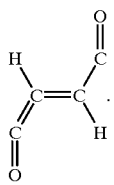

* * * * *